United States Patent
Fujita

(10) Patent No.: US 8,284,902 B2
(45) Date of Patent: Oct. 9, 2012

(54) RADIOGRAPHIC APPARATUS

(75) Inventor: Akinori Fujita, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 162 days.

(21) Appl. No.: 12/915,189

(22) Filed: Oct. 29, 2010

(65) Prior Publication Data

US 2011/0110500 A1    May 12, 2011

(30) Foreign Application Priority Data

Nov. 10, 2009   (JP) ................. 2009-256963

(51) Int. Cl.
*G21K 1/10* (2006.01)

(52) U.S. Cl. .................... 378/155; 378/98.12
(58) Field of Classification Search ........... 378/98.11, 378/98.12, 154, 155
See application file for complete search history.

(56) References Cited

U.S. PATENT DOCUMENTS

| | | | |
|---|---|---|---|
| 5,050,198 A | * | 9/1991 | Honda .................. 378/154 |
| 6,501,829 B2 | | 12/2002 | Matsumoto et al. |
| 7,110,502 B2 | * | 9/2006 | Tsuji .................... 378/155 |
| 7,142,705 B2 | * | 11/2006 | Inoue et al. ........... 378/154 |
| 2002/0196901 A1 | * | 12/2002 | Inoue .................... 378/154 |

FOREIGN PATENT DOCUMENTS

JP   2000-83951 A   3/2000
JP   2002-257939 A   9/2002

* cited by examiner

*Primary Examiner* — Glen Kao
(74) *Attorney, Agent, or Firm* — Cheng Law Group, PLLC

(57) ABSTRACT

In a radiographic apparatus, positions of a radiation grid and a radiation detector are determined such that, when a radiation source and the radiation detector are in a standard position, an arrangement pitch of shadows of absorbing foil strips appearing on a detecting plane of the radiation detector as a result of a radiation beam being emitted from the radiation source and blocked by the radiation grid is an integral multiple of an arrangement pitch in a transverse direction of radiation detecting elements. Further, the shadows of the absorbing foil strips appear without covering transversely adjacent pairs of the detecting elements.

20 Claims, 10 Drawing Sheets

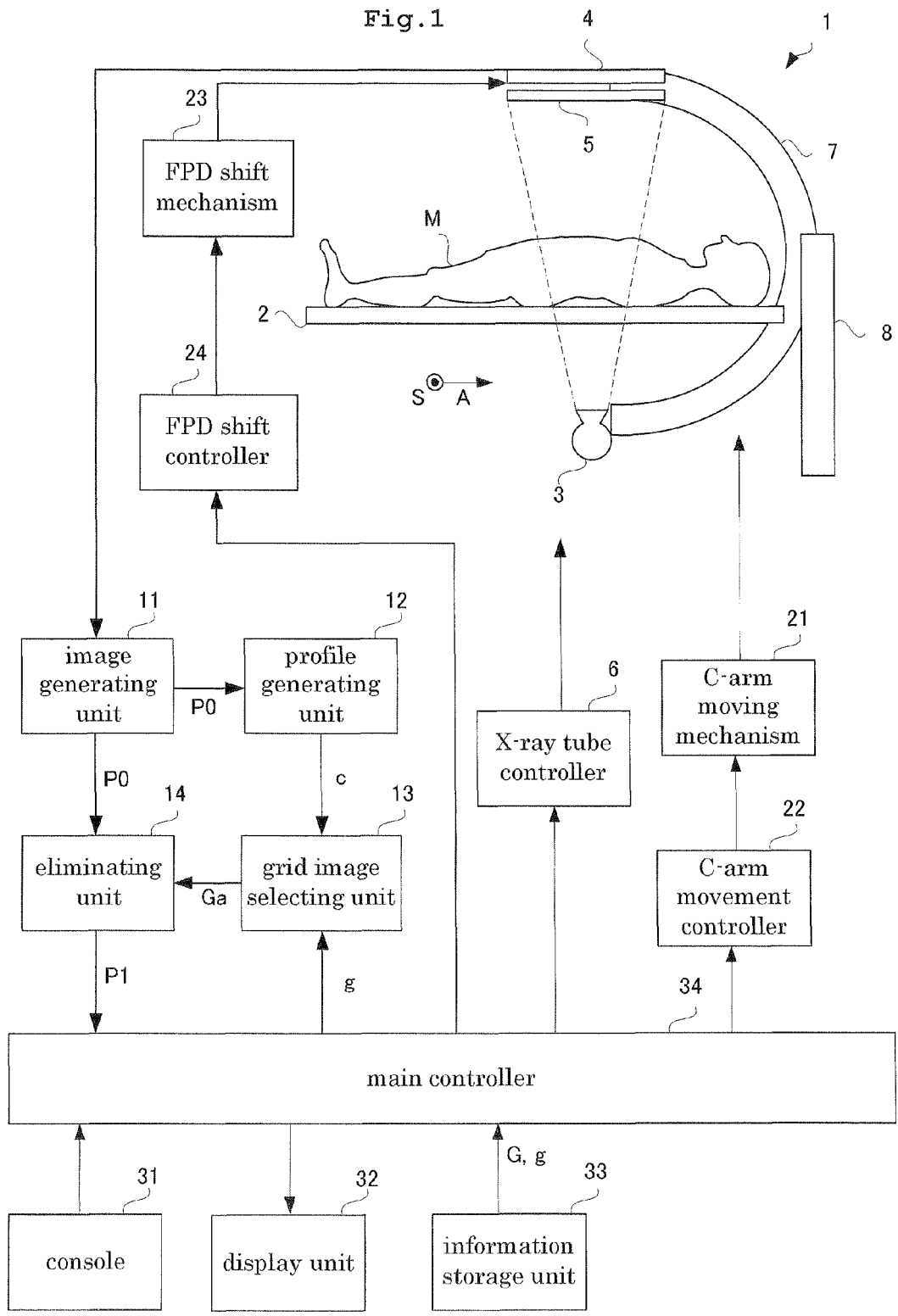

Fig.13
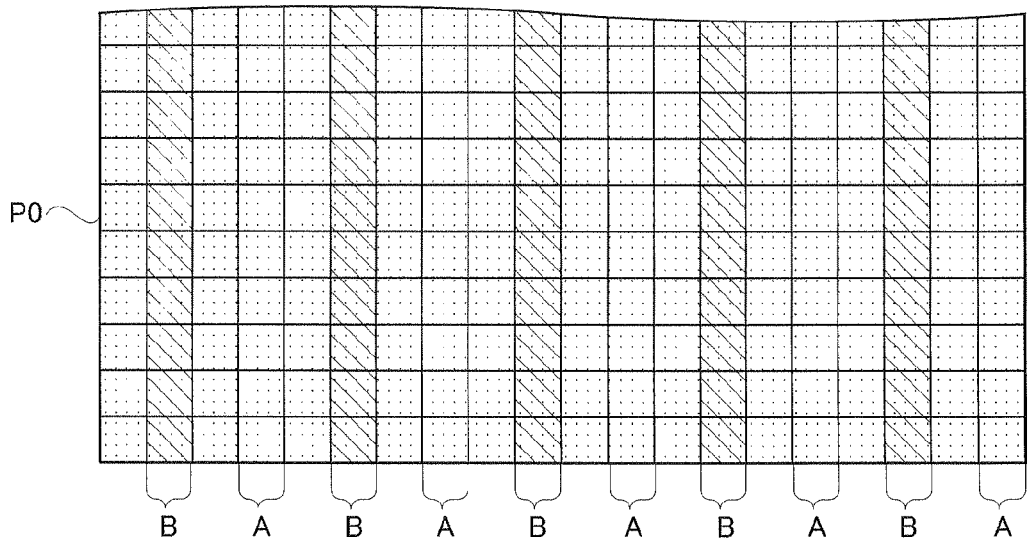
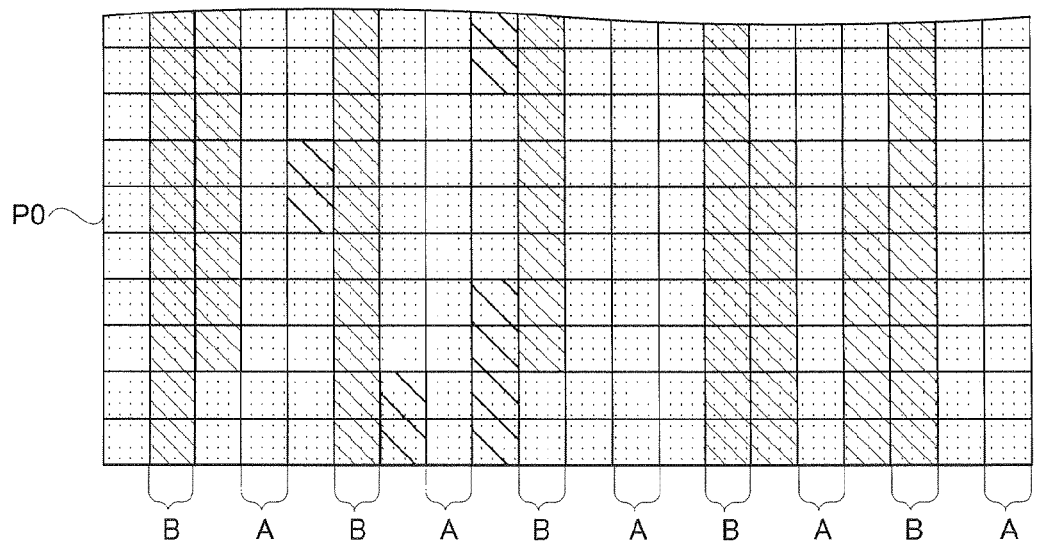

RADIOGRAPHIC APPARATUS

BACKGROUND OF THE INVENTION (1) Field of the Invention

This invention relates to a radiographic apparatus for acquiring fluoroscopic images of an object under examination by emitting radiation thereto, and more particularly to a radiographic apparatus having a radiation grid for removing scattered radiation generated in the object.

(2) Description of the Related Art

Medical institutions have radiographic apparatus installed therein for picking up fluoroscopic images of patients. As shown in FIG. 15, such a radiographic apparatus 51 includes a top board 52 for supporting a patient M, a radiation source 53 for emitting radiation, and a radiation detector 54 for detecting the radiation.

The radiation detector 54 has a radiation grid 55 placed on a radiation incidence plane (detecting plane) thereof for removing scattered radiation produced from the patient M. The radiation grid 55 has elongated strips of absorbing foil arranged as in a blind. When the scattered radiation strikes on the absorbing foil strips, most of the radiation is absorbed by the absorbing foil instead of reaching the radiation detector 54. Thus, the scattered radiation is absorbed and removed by the radiation grid 55.

The radiation grid 55 allows clear fluoroscopic images to be acquired free of the scattered radiation, but gives rise to the following problem. That is, shadows of the absorbing foil strips will fall on the radiation detector 54. Then, a striped pattern with dark pixel values will be reflected on a fluoroscopic image, which worsens visibility of the fluoroscopic image.

Some conventional radiographic apparatus are constructed to remove this striped pattern by image processing. That is, a conventional radiographic apparatus carries out a frequency analysis of a fluoroscopic image to remove the striped pattern. The striped pattern appearing on the fluoroscopic image has a plurality of dark lines arranged at constant intervals. When a frequency analysis is conducted on the fluoroscopic image, components the striped pattern will collect at a certain frequency. A fluoroscopic image free of the striped pattern will be acquired when a frequency inverse transform is carried out after a process for removing the frequency components. Such construction is described in detail in Japanese Unexamined Patent Publications No. 2000-83951 and No. 2002-257939.

Such a striped pattern removing method can be used also for a synchronous radiation grid. The synchronous radiation grid will be described hereinafter. The radiation detector 54 has detecting elements arranged in a matrix form on the detecting plane thereof for detecting radiation. The synchronous radiation grid is a radiation grid manufactured by arranging absorbing foil strips so that the pitch of the shadows of the absorbing foil strips falling on the radiation detector 54 may be an integral multiple of the pitch of the detecting elements (see Japanese Unexamined Patent Publications No. 2000-83951 and No. 2002-257939). When the synchronous radiation grid is used with a radiation source and a radiation detector set to a standard position, there will occur no moire due to interference between the pitch of the detecting elements and the pitch of the shadows of the absorbing foil strips. Thus, a fluoroscopic image can be acquired with less disturbance on the image due to the shadows of the absorbing foil strips. Even if the synchronous radiation grid is used, a striped pattern, though less conspicuous, still appears on the fluoroscopic image. This will be removed by frequency analysis.

However, the conventional radiographic apparatus has the following drawback.

According to the conventional radiographic apparatus, it is difficult to remove completely the striped pattern appearing on a fluoroscopic image. As shown in FIG. 15, where the radiation source 53 and radiation detector 54 are supported by a C-arm 57, a rotation of the C-arm 57 can incline the radiation source 53 and radiation detector 54 as maintained in the same relative position. When picking up images using such a radiographic apparatus, the operation is carried out while inclining the C-arm 57. The C-arm 57 can bend at this time to shift the relative position of the radiation source 53 and radiation detector 54 slightly. This will shift the position of the shadows of the absorbing foil strips appearing on the detecting plane of the radiation detector 54.

The conventional type radiation grid has the absorbing foil strips arranged in order with spacers such as of graphite interposed between the absorbing foil strips. These spacers absorb radiation to some extent. The synchronous radiation grid has nothing between adjacent absorbing foil strips, but it is hollow there to lessen the absorption of radiation. On the other hand, the absorbing foil strips can be distorted to deviate from accurate linearity because of the hollow structure. That is, winding shadows of the absorbing foil strips will be projected to the detecting plane of the radiation detector 54. Even so, the shadows of the absorbing foil strips are located in the middles in a transverse direction of the detecting elements. The shadow of each absorbing foil strip does not cover the detecting element pairs adjoining in the transverse direction, but appears in the fluoroscopic image as a vertical line having a width of one pixel.

If an image is picked up with the C-arm inclined from this state, the shadow of each absorbing foil strip will move in the transverse direction. Since the shadow of each absorbing foil strip is winding, the shadow will partly cover or will not cover adjacent detecting elements from the transverse direction. Then, the shadows of the absorbing foil strips appear as a complicated striped pattern on the fluoroscopic image. It is difficult to remove such a striped pattern by frequency analysis. The striped pattern becomes complicated, and difficult to remove uniformly by frequency analysis.

This invention has been made having regard to the state of the art noted above, and its object is to provide a radiographic apparatus which can reliably remove a striped pattern superimposed on a fluoroscopic image due to shadows of absorbing foil strips of a radiation grid falling on a radiation detector.

SUMMARY OF THE INVENTION

The above object is fulfilled, according to this invention, by a radiographic apparatus for acquiring radiological images, comprising a radiation source for emitting radiation; a radiation detector having a detecting plane with radiation detecting elements arranged in a matrix form thereon for detecting the radiation; an image generating device for generating images based on detection signals outputted from the radiation detector; a radiation grid placed to cover the detecting plane of the radiation detector, and having absorbing foil strips extending longitudinally and arranged transversely; a grid image storage device for storing a plurality of grid images picked up while varying positions in a transverse direction of the radiation source and the radiation detector, without an object under examination interposed between the radiation source and the radiation detector, the grid images having shadows of the radiation grid reflected thereon; an original image storage device for storing an original image picked up with the object under examination interposed between the radiation source and the radiation detector, the original image having a fluoroscopic image of the object under examination and the shadows of the absorbing foil strips of the radiation grid reflected thereon; a selecting device for selecting one grid image having a pattern most similar to a pattern of the shadows of the radiation grid reflected on the original image, from the plurality of grid images stored in the grid image storage device; and an eliminating device for eliminating the shadows of the absorbing foil strips from the original image based on the grid image selected by the selecting device; wherein the positions of the radiation grid and the radiation detector are determined such that, when the radiation source and the radiation detector are in a standard position, an arrangement pitch of the shadows of the absorbing foil strips appearing on the detecting plane of the radiation detector as a result of a radiation beam being emitted from the radiation source and blocked by the radiation grid is an integral multiple of an arrangement pitch in a transverse direction of the radiation detecting elements, and the shadows of the absorbing foil strips appear without covering transversely adjacent pairs of the detecting elements.

The radiographic apparatus according to this invention includes a synchronous radiation grid synchronized with the arrangement of the detecting elements of the radiation detector. That is, the arrangement pitch of the absorbing foil strips of the radiation grid is determined based on the arrangement pitch of the radiation detecting elements. Consequently, there occurs no moire due to interference between the arrangement of the shadows of the absorbing foil strips and the arrangement of the radiation detecting elements when the radiation source and the radiation detector are in the most frequently used standard position. This realizes generation of radiological images with improved visibility.

However, such synchronous radiation grid is liable to distortion of the absorbing foil strips. When the absorbing foil strips are distorted, it is difficult to predict a pattern of the shadows of the radiation grid appearing on the original image, and to remove the shadows of the radiation grid from the original image.

So, in this invention, a plurality of grid images are picked up beforehand, and a grid image most similar to the pattern of the shadows of the radiation grid appearing on the original image is selected, which is used to eliminate the pattern of the shadows of the radiation grid from the original image. That is, the pattern of the shadows of the radiation grid can be removed accurately from the original image after predicting in what shape the shadows of the radiation grid are reflected on the original image.

In the above radiographic apparatus, it is preferred that the grid images stored in the grid image storage device have been picked up while shifting the position of the radiation detector relative to the radiation source in the transverse direction.

According to the above construction, the grid images can be picked up with increased appropriateness. When the positional relationship between the radiation source and radiation detector shifts in the transverse direction, a major change will occur with the pattern of the shadows of the radiation grid appearing on the original image. So, in the above construction, the grid images are picked up beforehand while shifting the position of radiation detector relative to the radiation source in the transverse direction. Then, even if the positional relationship between the radiation source and radiation detector shifts in the transverse direction at the time of original image acquisition, the pattern of the shadows of the radiation grid appearing on the original image can be selected from the already procured grid images. This allows the pattern of the shadows of the radiation grid appearing on the original image to be predicted accurately.

In the above radiographic apparatus, it is preferred that the grid images stored in the grid image storage device have been picked up without anything placed between the radiation source and the radiation grid.

According to the above construction, the grid images can be picked up with increased appropriateness. With this construction, since only the shadows of the radiation grid are reflected on the grid images, the pattern of the shadows of the radiation grid appearing on the original image is expressed accurately.

In the above radiographic apparatus, it is possible that the grid images stored in the grid image storage device have been picked up with a phantom, which generates scattered rays, placed between the radiation source and the radiation grid.

According to the above construction, the grid images can be picked up with increased appropriateness. The original image includes scattered ray components generated from the object under examination, and the pattern of the shadows of the radiation grid appearing on the original image also changes under the influence of scattered rays. Therefore, the shadows of the radiation grid appearing on the original image can be grasped with increased accuracy by picking up the grid images in a state of scattered rays being generated. This arrangement enables acquisition of grid images that anticipate the influence of scattered rays.

It is preferred that the above radiographic apparatus further comprises a profile generating device for generating profiles each having pixel values arranged in a row in the transverse direction of the radiation grid, based on images each having pixel values arranged in two dimensions; wherein the selecting device is arranged to select the one grid image using an original image profile generated from the original image, and grid profiles generated from the grid images.

The above arrangement represents details of a method of selecting a grid image. That is, similarity between the original image and grid images is determined without using the images per se, and is determined using profiles showing characteristics of the shadows of the radiation grid reflected on the images. The profiles have pixel values arranged in a row, whereby the profiles can be compared at high speed. Therefore, also in an examination in which original images are picked up continuously, the shadows of the radiation grid can be removed from the original images reliably.

In the above radiographic apparatus, it is preferred that the profile generating device is arranged to generate an estimated profile from the original image profile when the radiation grid is not reflected on the original image, and generate a profile for comparison by subtracting the estimated profile from the original image profile, wherein the selecting device is arranged to select one grid image by selecting a grid profile most similar to the profile for comparison.

The above arrangement represents details of a method of selecting a grid image. That is, the original image has an image of the object under examination and the shadows of the radiation grid overlapping each other. When the profile of the original image is used as it is for comparison of the profiles, the components of the object image superimposed on the profile of the original image will baffle a determination of similarity between the profiles. In view of such a situation, this invention generates, from the original image profile, a profile for comparison without the object image reflected on the original image, and by using this for comparison with the grid profiles, a determination is made of similarity between the profiles. Consequently, the shadows of the radiation grid reflected on the original image can be grasped with increased reliability.

In the above radiographic apparatus, it is preferred that the selecting device is arranged to determine similarity between the profile for comparison and the grid profiles by a correlational method.

The above arrangement represents a specific method of determining similarity between the profiles. By carrying out comparison using the correlational method which obtains correlation coefficients of both profiles, the shadows of the radiation grid reflected on the original image can be grasped with increased reliability.

The radiographic apparatus according to this invention includes a synchronous radiation grid which is liable to distortion of the absorbing foil strips. When the absorbing foil strips are distorted, it is difficult to remove the shadows of the radiation grid from the original image. So, in this invention, a plurality of grid images are picked up beforehand, and an appropriate grid image is selected therefrom, which is used to eliminate the pattern of the shadows of the radiation grid from the original image. According to this invention, the pattern of the shadows of the radiation grid can be removed accurately from the original image.

It is preferred that the above radiographic apparatus further comprises a C-arm for supporting the radiation source and the radiation detector.

The above represents a specific construction of this invention. With this construction, the radiation source and radiation detector can be moved while maintaining a positional relationship therebetween.

In the above radiographic apparatus, it is preferred that the radiation grid is a synchronous grid with an arrangement of the absorbing foil strips synchronized with an arrangement of the detecting elements of the radiation detector.

The above represents a specific construction of this invention. This invention is applicable to what is called a synchronous grid.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

FIG. 1 is a functional block diagram illustrating a construction of an X-ray apparatus according to Embodiment 1;

FIG. 13 is a schematic view illustrating an original image according to Embodiment 1;

DESCRIPTION OF THE PREFERRED EMBODIMENTS

Figure 2A:
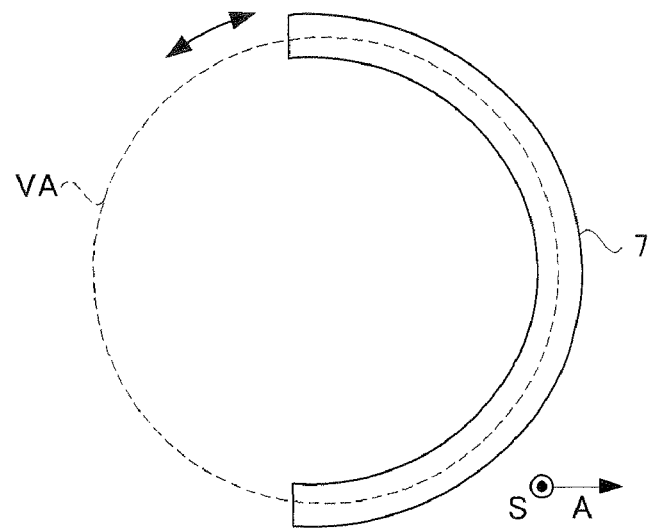
FIG. 2A is a schematic view illustrating movement of a C-arm according to Embodiment 1.

An embodiment of this invention will be described hereinafter. X-rays in the embodiment correspond to the radiation in this invention.

<Construction of X-ray Apparatus>

As shown in FIG. 1, an X-ray apparatus 1 in Embodiment 1 includes a top board 2 for supporting a patient M, an X-ray tube 3 disposed below the top board 2 for emitting X-rays, a flat panel detector (FPD) 4 disposed above the top board 2 for detecting X-rays, an X-ray tube controller 6 for controlling a tube current and tube voltage of the X-ray tube 3, a C-arm 7 for supporting the X-ray tube 3 and FPD 4, a strut 8 for supporting the C-arm 7, a C-arm moving mechanism 21 for moving the C-arm 7, and a C-arm movement controller 22 for controlling the C-arm moving mechanism 21. The X-ray tube 3 corresponds to the radiation source in this invention. The FPD 4 corresponds to the radiation detector in this invention.

Figure 2B:
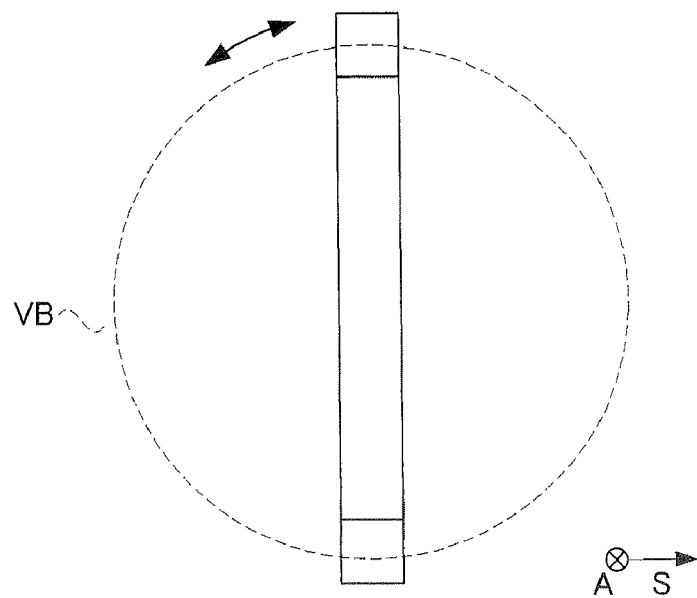
FIG. 2B is a schematic view illustrating movement of the C-arm according to Embodiment 1.

By the C-arm moving mechanism 21, the C-arm 7 is rotatable as well as movable vertically and horizontally. That is, the C-arm 7 is rotatable along an imaginary circle VA along which the curved C-arm 7 extends as shown in FIG. 2A, and is also rotatable to move opposite ends thereof along an imaginary circle VB on a plane perpendicular to a projecting direction (the direction A along the body axis) in which the opposite ends of the C-arm 7 project from the strut 8 as shown in FIG. 2B.

Figure 3:
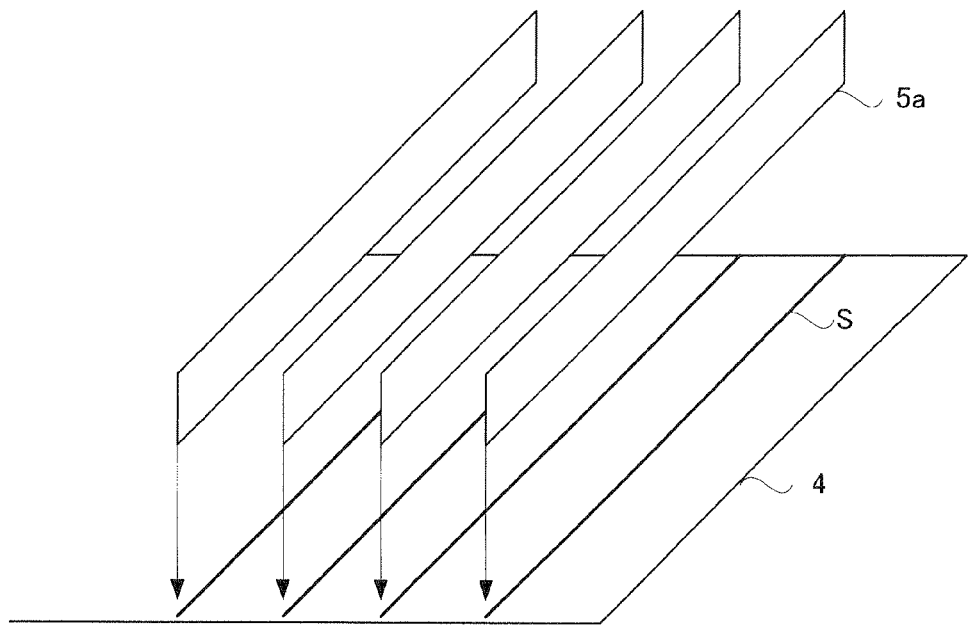
FIG. 3 is a perspective view illustrating a construction of an X-ray grid according to Embodiment 1.

An X-ray grid 5 is provided to cover an X-ray detecting plane of the FPD 4. FIG. 3 is a perspective view illustrating the construction of the X-ray grid 5 in Embodiment 1. As shown in FIG. 3, the X-ray grid 5 in Embodiment 1 has absorbing foil strips 5a extending longitudinally. The absorbing foil strips 5a are arranged transversely and, when seen as the entire X-ray grid 5, are arranged as in a blind. The arrangement pitch is 400 µm, for example. The absorbing foil strips 5a are formed of a molybdenum alloy, a tantalum alloy or the like which absorbs X-rays. The X-ray grid 5 corresponds to the radiation grid in this invention.

An FPD shift mechanism 23 is provided to move the FPD 4 toward and away from the X-ray tube 3. This can adjust an enlargement ratio of a patient image falling on the FPD 4. An FPD shift controller 24 is provided to control the FPD shift mechanism 23. When the FPD 4 is moved by the FPD shift mechanism 23, the X-ray grid 5 will also be moved therewith.

Figure 4:
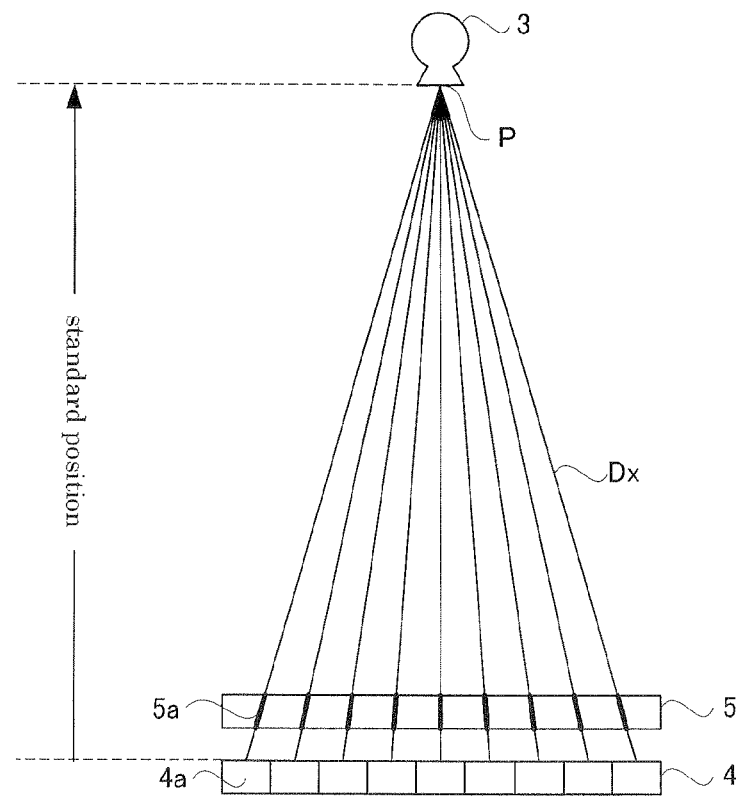
FIG. 4 is a schematic view illustrating a positional relationship between the X-ray grid, an FPD and an X-ray tube according to Embodiment 1.

A positional relationship between the FPD 4 and X-ray grid 5 will be described. FIG. 4 shows a positional relationship between the X-ray grid 5/FPD 4 and the X-ray tube 3. X-rays Dx are emitted from a focus P of the X-ray tube 3. Although the absorbing foil strips 5*a* of FIG. 3 appear to be arranged in parallel, they are in practice arranged at slightly varied angles to align with the X-rays Dx emitted. The positional relationship in which shadows S of the absorbing foil strips 5*a* fall on the middles of the detecting elements 4*a* of the FPD 4 is called a standard position.

Figure 5:
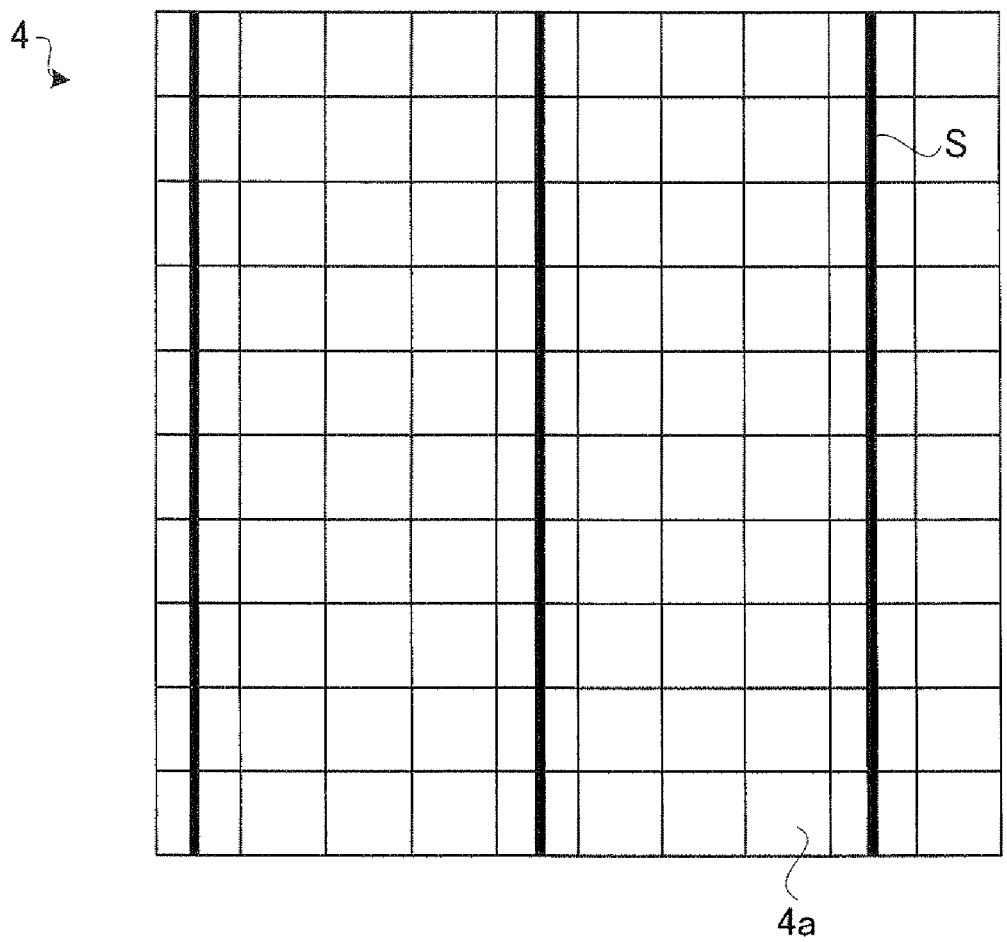
FIG. 5 is a plan view illustrating the construction of the X-ray grid according to Embodiment 1.

As shown in FIG. 5, the detecting elements 4*a* which detect X-rays are arranged longitudinally and transversely on the X-ray detecting plane of the FPD 4. When X-rays are emitted from the X-ray tube 3, shadows S of the absorbing foil strips 5*a* of the X-ray grid 5 will fall on certain of the detecting elements 4*a* of the FPD 4. At this time, as shown in FIG. 5, the shadows S are located at the middles in the transverse direction of the certain detecting elements 4*a*. Therefore, the shadows S of the absorbing foil strips 5*a* appear without covering detecting elements 4*a* adjoining these detecting elements 4*a* in the transverse direction. Moreover, the arrangement pitch in the transverse direction of the shadows S is an integral multiple (fourfold in the embodiment) of the arrangement pitch of the detecting elements 4*a* of the FPD 4. Thus, the positions of the absorbing foil strips 5*a* over the FPD 4 and the arrangement pitch in the transverse direction of the absorbing foil strips 5*a* are determined with reference to each of the positions of the shadows S and detecting elements 4*a* and the arrangement pitch in the transverse direction of the detecting elements 4*a*. The X-ray grid 5 with such arrangement pitch of the absorbing foil strips 5*a* adjusted to the arrangement pitch of the detecting elements 4*a* is called a synchronous X-ray grid. The detecting elements 4*a* correspond to the radiation detecting elements in this invention.

However, when the C-arm 7 rotates as in FIG. 2, the shadows S of the absorbing foil strips 5*a* of the X-ray grid 5 will shift from the middles in the transverse direction of the detecting elements 4*a* of the FPD 4. The X-ray tube 3 is a heavy object, and the C-arm 7 supporting the X-ray tube 3 is liable to bend. This bending becomes larger as the X-ray tube 3 moves farther away from the strut 8. The state of the FPD 4 and shadows S shown in FIG. 5 occurs when the X-ray tube 3 is directly under the FPD 4 as shown in FIG. 1.

Also when the FPD shift mechanism 23 moves the FPD 4 toward or away from the X-ray tube 3, the shadows S of the absorbing foil strips 5*a* of the X-ray grid 5 will shift from the middles in the transverse direction of the detecting elements 4*a* of the FPD 4. This is because the enlargement ratio of the X-ray grid 5 on the FPD 4 will be changed when the FPD 4 is moved toward or away from the X-ray tube 3. The FPD 4 and shadows S are in the state shown in FIG. 5 when the X-ray tube 3 and FPD 4 are at a predetermined standard distance from each other.

The situation where the X-ray tube 3 and FPD 4 in Embodiment 1 are in the standard position refers to a situation where the X-ray tube 3 is directly under FPD 4 as shown in FIG. 1 and the X-ray tube 3 and FPD 4 are at the standard distance from each other. See FIG. 4 for specific illustration. At this time, the shadows S are located at the middles in the transverse direction of certain detecting elements 4*a* as shown in FIG. 5.

As shown in FIG. 1, the X-ray apparatus 1 according to Embodiment 1 includes an image generating unit 11 for generating various images, a profile generating unit 12 for generating a profile c for comparison, a grid image selecting unit 13 for selecting one of grid images G, an eliminating unit 14 for removing shadows of the X-ray grid 5 from an original image P0, a console 31 for inputting operator's instructions, a display unit 32 for displaying corrected images, and an information storage unit 33 for storing a variety of information. The eliminating unit 14 corresponds to the eliminating device in this invention. The image generating unit 11 corresponds to the image generating device in this invention. The profile generating unit 12 corresponds to the profile generating device in this invention. The grid image selecting unit 13 corresponds to the selecting device in this invention. The information storage unit 33 corresponds to the grid image storage device and original image storage device in this invention.

The X-ray apparatus 1 according to Embodiment 1 includes also a main controller 34 for performing overall control of the components 6, 11, 12, 13, 14, 22 and 24. The main controller 34 has a CPU, and realizes the above components by executing various programs. The above components may be divided into arithmetic units which perform their functions.

The information storage unit 33 serves to store grid images G and original image P0 described hereinafter. This information storage unit 33 stores all of various parameters referred to for control of the X-ray apparatus 1, such as a tube voltage, tube current and pulse width used in control by the X-ray tube controller 6, for example.

The grid images G will now be described. The grid images G are images of the X-ray grid 5 provided for the FPD 4 which are picked up with X-rays, and 189 such images are stored in the information storage unit 33. These grid images G are acquired with the X-ray tube 3 and FPD 4 detached from the C-arm 7. That is, the grid images G are acquired by emitting X-rays toward the FPD 4 with the X-ray grid 5 attached thereto.

Figure 6:
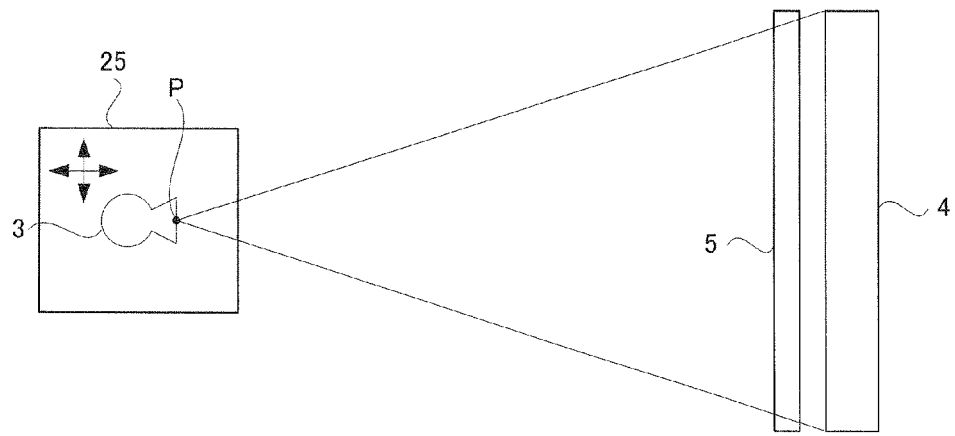
FIG. 6 is a schematic view illustrating a method of acquiring grid images according to Embodiment 1.

A method of picking up the grid images G will be described. When picking up the grid images G, as shown in FIG. 6, the X-ray tube 3 for emitting X-rays is placed on a stage 25 which moves the X-ray tube 3 in the transverse direction of the X-ray grid 5. With this arrangement, the X-ray tube 3 can be moved in the transverse direction relative to the FPD 4 from the state of the X-ray tube 3 and FPD 4 being in the standard position. The stage 25 can also move the X-ray tube 3 toward and away from the FPD 4. Therefore, the X-ray tube 3 can be moved toward or away from the FPD 4, from the state of the X-ray tube 3 and FPD 4 being in the standard position. Thus, the stage 25 for receiving the X-ray tube 3 acts as an XY stage movable in two perpendicular directions.

How the grid images G are picked up will be described. To pick up a grid image G, X-rays are first emitted from the X-ray tube 3. Then, shadows of the X-ray grid 5 fall on the FPD 4. The image generating unit 11 receives detection data from the FPD 4, and generates a grid image G having the shadows of the X-ray grid 5. This grid image G is stored in the information storage unit 33.

Such image pickup is carried out a plurality of times while sliding the X-ray tube 3 in the transverse direction. That is, the X-ray tube 3 is moved in the transverse direction by the stage 25, and after once stopping the movement, an image of the X-ray grid 5 is picked up again. Such movement and image pickup of the X-ray grid 5 are repeated to pick up one grid image G after another.

How the X-ray tube 3 is moved during the operation for picking up the grid image G will be described. It is assumed that FIG. 6 shows the positional relationship between the X-ray tube 3 and FPD 4 in the standard position. Sign P in the figure denotes the focus of an X-ray beam emitted from the X-ray tube 3. Since the grid images G are picked up successively while moving the X-ray tube 3, the position of the focus of the X-ray tube 3 relative to the FPD 4 also shifts in successive steps.

Figure 7:
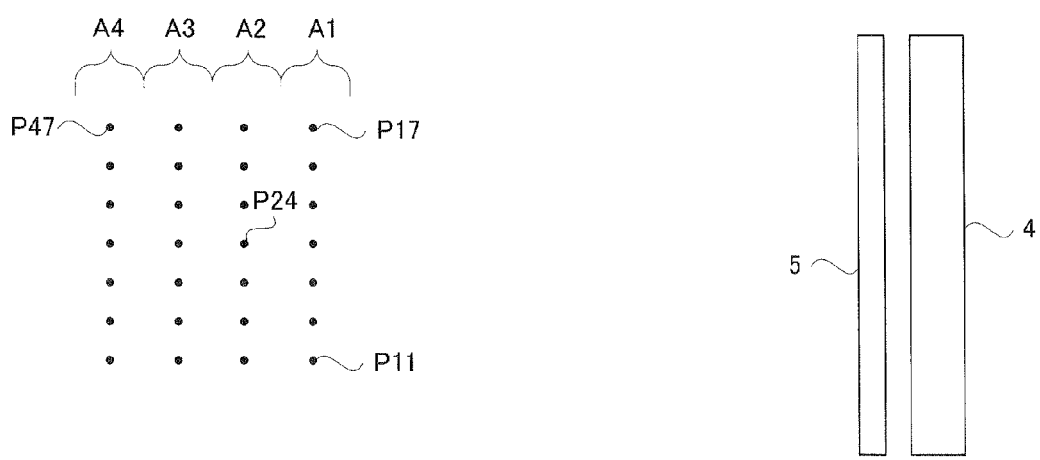
FIG. 7 is a schematic view illustrating the method of acquiring the grid images according to Embodiment 1.

The focal position of the X-ray tube 3 at the time an X-ray grid image G is picked up is one of positions P11-P47 shown in FIG. 7. To pick up X-ray grid images, while the focus of the X-ray tube 3 is first moved in the transverse direction from the standard position indicated by P24, image pickup is carried out in the seven focal positions indicated by A2 in FIG. 7. Then, after the focus of the X-ray tube 3 is moved toward the FPD 4, image pickup is carried out while the focus is moved in the transverse direction. Consequently, an X-ray grid image is picked up in each of the focal positions P11-P17 indicated by A1 in FIG. 7. Similarly, after the focus of the X-ray tube 3 is moved away from the FPD 4, image pickup is carried out while the focus is moved in the transverse direction, to pick up an X-ray grid image in each of the seven focal positions indicated by A3 or A4 in FIG. 7. For simplicity of description, FIG. 7 shows the case of image pickup through four layers each including seven focal positions, to pick up X-ray grid images in a total of 28 focal positions. In an actual operation of Embodiment 1, image pickup is carried out through 21 layers each including nine focal positions, to pick up X-ray grid images in a total of 189 focal positions.

The acquired X-ray grid images G will be described briefly. When the X-ray tube 3 is in the standard position (when the focus of the X-ray tube 3 is at P24 in FIG. 7), the shadows S of the absorbing foil strips 5a fall on the FPD 4 as shown in the left portion of FIG. 8. At this time, an X-ray grid image G presents dark lines with the width of one pixel as shown in the right portion of FIG. 8. Since the absorbing foil strips 5a are twisted or bent, their shadows S are distorted to some extent. When the absorbing foil strips 5a are twisted, for example, the shadows S have varying widths in the transverse direction. Under the influence of this variation, the dark lines appearing on the X-ray grid image G have a partial unevenness of darkness as shown in the right portion of FIG. 8.

Figure 8:
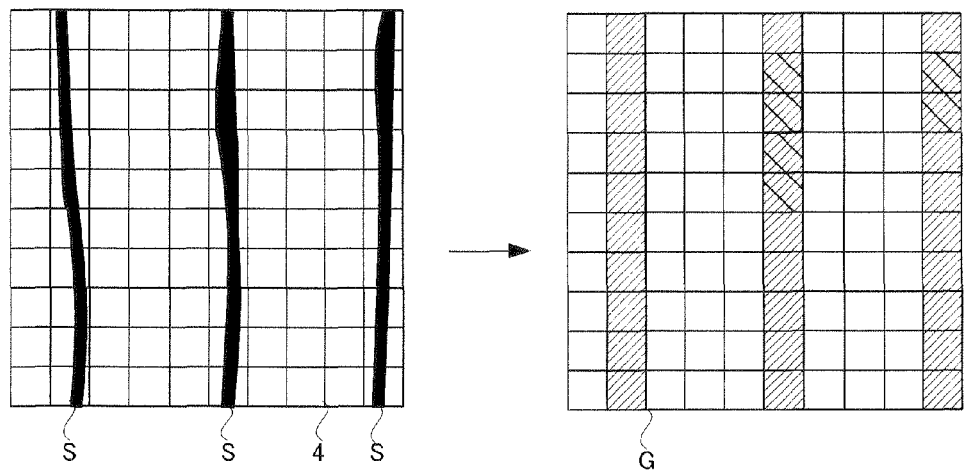
FIG. 8 is a schematic view illustrating a grid images according to Embodiment 1.
Figure 9:
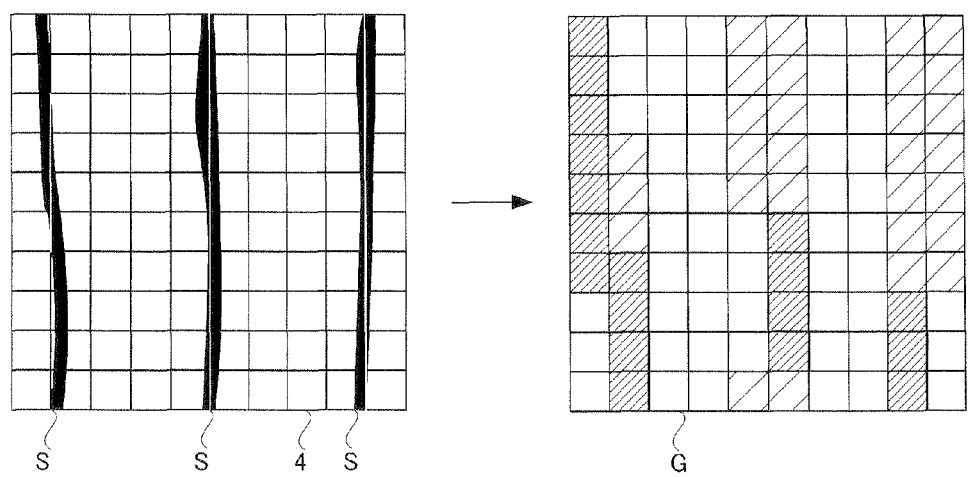
FIG. 9 is a schematic view illustrating a grid image according to Embodiment 1.

When the X-ray tube 3 is moved from the standard position, the shadows S of the absorbing foil strips 5a will fall on the FPD 4 as transversely shifted from the state in FIG. 8, as shown in the left portion of FIG. 9. Since the shadows S of the absorbing foil strips 5a are distorted, the shadows S partly straddle or do not straddle the detecting elements 4a in the transverse direction. The X-ray grid image G at this time presents dark lines of complicated shape as shown in the right portion of FIG. 9. Where the shadows S straddle the detecting elements 4a, the shadows S are distributed to the transversely adjacent detecting elements 4a, resulting in dark lines having a width corresponding to two pixels on the X-ray grid image G. Where the shadows S do not straddle the detecting elements 4a, the width of the dark lines appearing on the X-ray grid image G remains to be that of one pixel.

Figure 10:
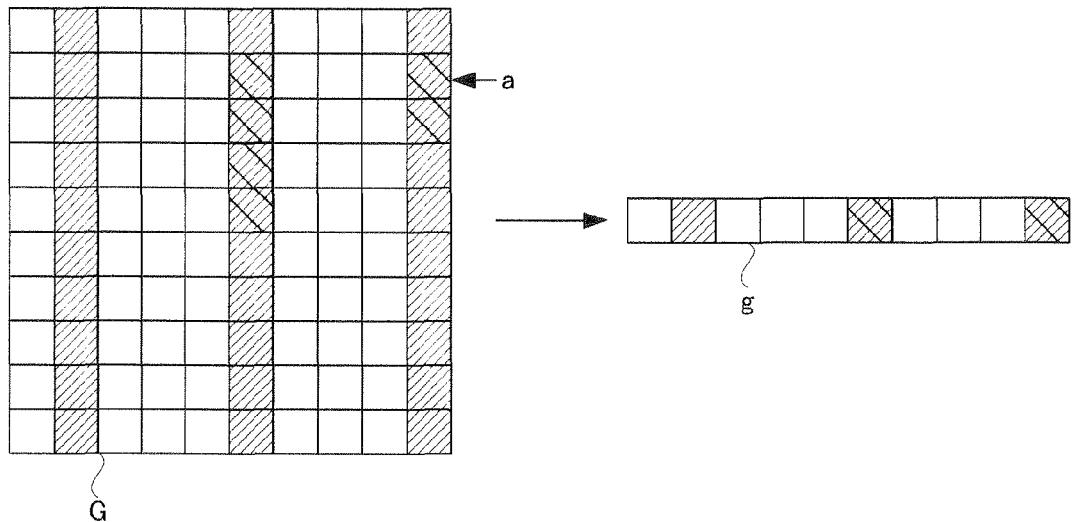
FIG. 10 is a schematic view illustrating a grid profile according to Embodiment 1.

The X-ray grid image G, after information concerning a positional relationship between the X-ray tube 3 and FPD 4 at the time of image pickup is applied thereto by the image generating unit 11, is outputted to the profile generating unit 12. The profile generating unit 12 converts the X-ray grid image G in the form of a two-dimensional image into one-dimensional data. That is, the profile generating unit 12, as shown in FIG. 10, averages pixel values located in each line in the longitudinal direction among the pixel values constituting the X-ray grid image G, and generates a grid profile g with the average values arranged in the transverse direction. In another method of generating the grid profile g, a group of pixel values arranged in one row in the transverse direction may be extracted by selecting a certain position in the longitudinal direction of the X-ray grid image G as indicated by arrow a in FIG. 10. The profile generating unit 12 stores the X-ray grid image G and the grid profile g generated based thereon, as related to each other, in the information storage unit 33. Thus, 28 (actually 189) X-ray grid images G will be stored, together with grid profiles g related thereto, in the information storage unit 33.

<Operation of X-ray Apparatus>

Figure 11:
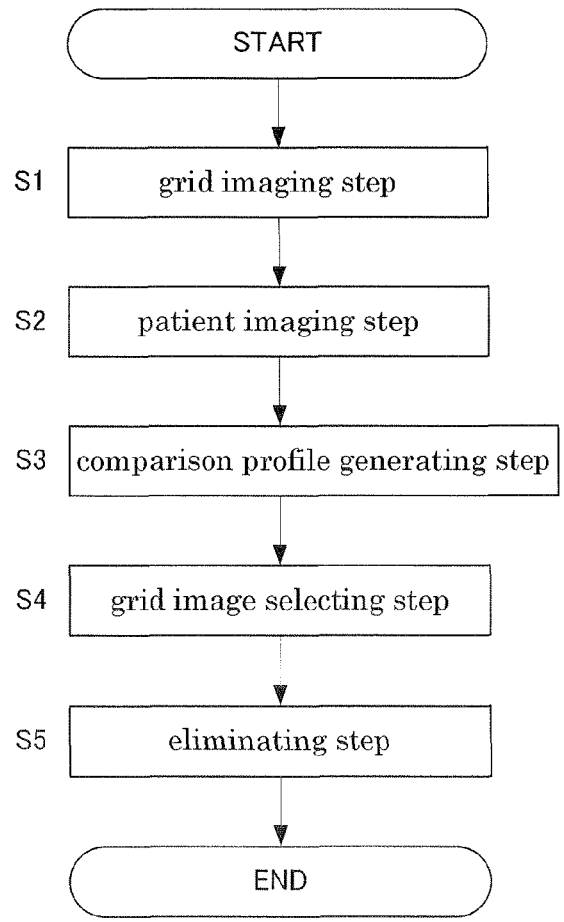
FIG. 11 is a flow chart illustrating operation according to Embodiment 1.

Operation of the X-ray apparatus 1 will be described next. In carrying out an examination with the X-ray apparatus 1 in Embodiment 1, as shown in FIG. 11, images of the X-ray grid 5 are picked up to acquire a plurality of grid images G beforehand (grid imaging step S1). Then, a patient M is placed on the top board 2, and an original image P0 of the patient M is acquired (patient imaging step S2). A profile c for comparison is acquired based on the original image P0 (comparison profile generating step S3). Then, a comparison is made between the profile c for comparison and the grid images G (their profile data, to be exact), to select a grid image G having the striped pattern most similar to that of the shadows of the X-ray grid 5 appearing on the original image P0 (grid image selecting step S4). Finally, the striped pattern of the shadows of the X-ray grid 5 is eliminated from the original image P0 using the selected grid image G (eliminating step S5). These steps will be described in order hereinafter.

<Grid Imaging Step S1 and Patient Imaging Step S2>

First, images of the X-ray grid 5 are picked up with the X-ray tube 3 placed on the stage 25. It is sufficient to execute this step once before shipment of the X-ray apparatus 1. Therefore, an actual examination of the patient M begins when the patient M is placed on the top board 2 and an X-ray beam is emitted toward the patient M (patient imaging step S2). The FPD 4 detects the X-ray beam transmitted through the patient M, and outputs detection data to the image generating unit 11. The image generating unit 11, by arranging the detection data in two dimensions, for example, acquires an original image P0 showing both a fluoroscopic image of the patient M and shadows of the X-ray grid 5.

<Comparison Profile Generating Step S3: Generation of Original Image Profile p>

The original image P0 is outputted to the profile generating unit 12. The profile generating unit 12 generates an original image profile p, which is a profile of the original image P0, in the same way as generating the grid profiles g. The original image profile p is acquired by averaging pixel values or extracting from a pixel value group arranged in one row in the transverse direction of the original image P0. The original image profile p, as shown in the upper portion of FIG. 12A, consists of a superimposition of two parts which are components derived from the shadows S of the absorbing foil strips 5a shown with slashes, and components derived from the fluoroscopic image of the patient M shown with halftone dots.

<Comparison Profile Generating Step S3: Extraction of Areas A>

Figure 12A:
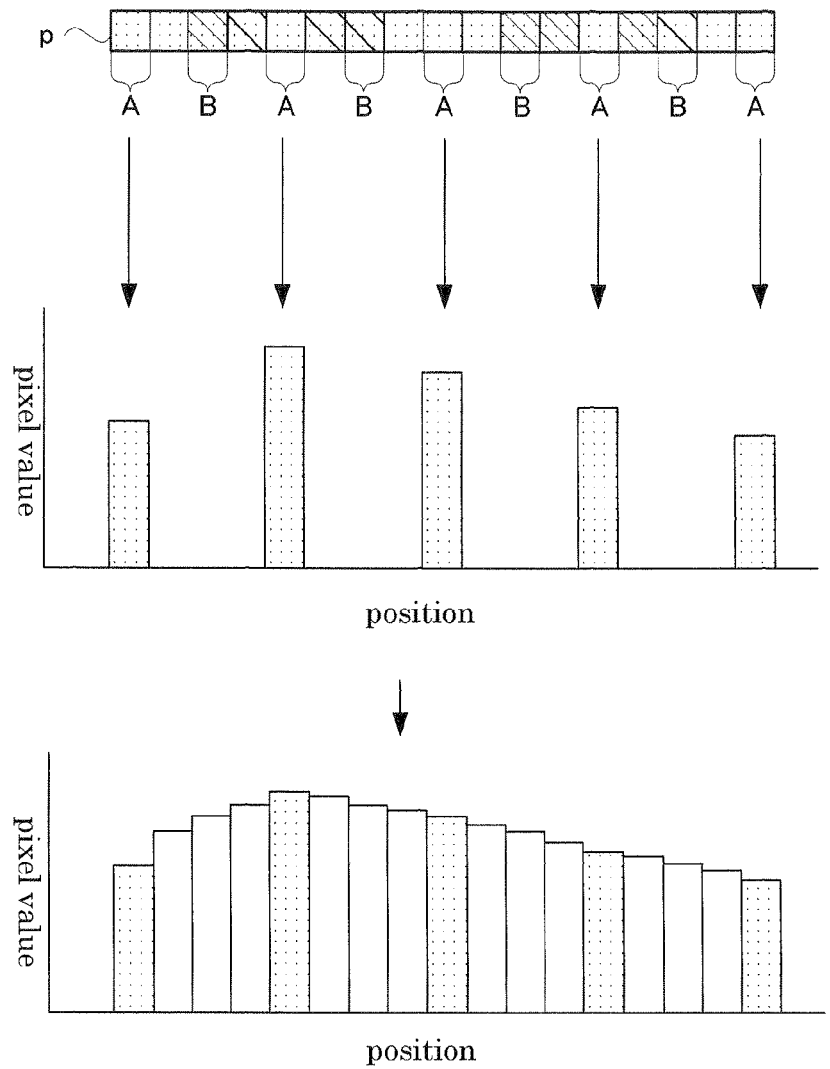
FIG. 12A is a schematic view illustrating a method of acquiring a profile for comparison according to Embodiment 1.

The profile generating unit 12 extracts only pixels from areas A of the original image profile p shown in the upper portion of FIG. 12A. The areas A will be described. Assume that areas B are where the shadows S of the absorbing foil strips 5a fall when the X-ray tube 3 and FPD 4 are in the standard position. The areas A are areas spaced from the areas B by two pixels in the transverse direction on the original image profile p. The middle portion of FIG. 12A expresses pixel values of the extracted areas A in a bar chart. The areas A are areas positively free from the shadows S of the absorbing foil strips 5a, as described hereinafter. If, on comparison, differences in pixel value are found among the areas A, such differences are not caused by the shadows S of the absorbing foil strips 5a, but are due to components of the fluoroscopic image of the patient M. That is, the profile generating unit 12 extracts only pixels from the areas A, and this results in extraction of a pixel group including only components of the patient image reflected on the original image profile p.

The reason why the areas A include only components of the patient image will be explained. FIG. 13 is a schematic view of shadows of the absorbing foil strips 5a appearing on the original image P0. When the X-ray tube 3 and FPD 4 are in the standard position, as shown in the upper portion of FIG. 13, the shadows S of the absorbing foil strips 5a appear in the areas B having the width of one pixel. The areas B occur repeatedly in the transverse direction, forming a striped pattern when the original image P0 is seen as a whole. In FIG. 13, the original image P0 consists of a superimposition of two parts which are components derived from the shadows S of the absorbing foil strips 5a shown with slashes, and components derived from the fluoroscopic image of the patient M (components of the patient image) shown with halftone dots. The fluoroscopic image of the patient M shown with halftone dots, in practice, is that of internal organ tissue, bone tissue or the like of the patient M.

When the relative position between the X-ray tube 3 and FPD 4 shifts from the standard position, as shown in the lower portion of FIG. 13, the shadows S of the absorbing foil strips 5a will appear as protruding from the areas B. However, the shadows S of the absorbing foil strips 5a will never appear in the areas A shown in FIG. 13. To whatever extent the positional relationship between the X-ray tube 3 and FPD 4 may change during the operation to pick up an image of the patient M, the distance of movement in the transverse direction of the shadows S of the absorbing foil strips 5a on the original image P0 is less than a distance corresponding to one pixel. Thus, the shadows S of the absorbing foil strips 5a will not move to the areas A spaced from the areas B by two pixels in the transverse direction.

Its reason will be explained. The relative position between the X-ray tube 3 and FPD 4 is shiftable about 2 mm by bending of the C-arm 7. When in the standard position, the distance between the X-ray tube 3 and FPD 4 is about 1,000 mm, and the distance between the X-ray grid 5 and FPD 4 is 20 mm. Based on these figures, when the relative position between the X-ray tube 3 and FPD 4 shifts 2 mm in the transverse direction of the X-ray grid 5, the shadows S of the absorbing foil strips 5a will move 40 µm in the transverse direction. The width in the transverse direction of the shadows S of the absorbing foil strips 5a is about 30 µm. The width in the transverse direction of the detecting elements 4a arranged on the detecting plane of FPD 4 is 100 µm, although there are certain variations. It may therefore be said that the shadows S of the absorbing foil strips 5a present in the areas B of the original image P0 can never move as far as the areas A at a distance of 100 µm or more.

<Comparison Profile Generating Step S3: Generation of Estimated Profile sp>

Figure 12B:
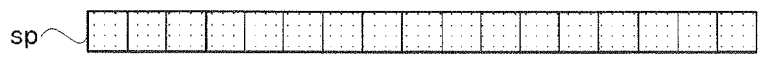
FIG. 12B is a schematic view illustrating the method of acquiring the profile for comparison according to Embodiment 1.

After extracting the areas A, the profile generating unit 12 interpolates pixel values in order to grasp components of the patient image over the entire area of the original image profile p. That is, the profile generating unit 12, using the pixel values of the areas A, estimates pixel values for the three pixels which should lie between adjacent areas A. The method carried out by the profile generating unit 12 for estimating pixel values may be a spline interpolation method, for example. The lower portion of FIG. 12A shows a state of the time when this operation is finished. In the lower portion of FIG. 12A, the pixel values estimated by the profile generating unit 12 are shown as bars without halftone dots for distinction. FIG. 12B shows this estimated profile sp expressed as one-dimensional data. The estimated profile sp is formed only of fluoroscopic image components of the patient M shown with halftone dots.

<Comparison Profile Generating Step S3: Generation of Profile c for Comparison>

Figure 12C:
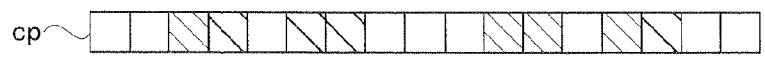
FIG. 12C is a schematic view illustrating the method of acquiring the profile for comparison according to Embodiment 1.

The profile generating unit 12, by subtracting the estimated profile sp from the original image profile p, generates the profile c for comparison for use in profile comparison. The profile c for comparison is formed only of components of the shadows S of the absorbing foil strips 5a shown with slashes as in FIG. 12C.

<Grid Image Selecting Step S4>

The profile c for comparison is outputted to the grid image selecting unit 13. This profile c for comparison expresses a pattern of the shadows of the X-ray grid 5 appearing on the original image P0. There should be, in the information storage unit 33, grid profiles g having similar patterns to the profile c for comparison. The grid image selecting unit 13 selects a grid profile g having the most similar pattern to that of the profile c for comparison.

Details of an operation for selection of a grid profile g will be described. The grid image selecting unit 13 first selects grid images G roughly. Distance information of the X-ray tube 3 and FPD 4 has already been sent to the grid image selecting unit 13 from the FPD shift controller 24. The grid image selecting unit 13 selects one of A1-A4 in FIG. 7 to which the position of the X-ray tube 3 relative to the FPD 4 was close at the time the original image P0 was picked up. Assume that the grid image selecting unit 13 selects A1 at this time, for example. The grid image selecting unit 13 reads from the information storage unit 33 the seven X-ray grid images G (their profile grid profiles g, to be exact) picked up when the focus of the X-ray tube 3 in the positions of A1.

The grid image selecting unit 13 selects one X-ray grid image G from the seven X-ray grid images G through comparison between the profiles g and c. Specifically, the grid profiles g of the seven X-ray grid images G are successively applied to the profile c for comparison, to obtain correlation coefficients h and select a grid image G. These correlation coefficients h are indexes showing degrees of coincidence between the grid profiles g and the profile c for comparison. The larger correlation coefficient h shows the higher degree of coincidence. The grid profiles g and the profile c for comparison express patterns of the shadows of the X-ray grid 5 appearing on the grid images G and original image P0. Therefore, a large correlation coefficient h of the profiles indicates that the pattern of the shadows of the X-ray grid 5 appearing on a grid image G is similar to the pattern of the shadows of the X-ray grid 5 appearing on the original image P0.

A method by which the grid image selecting unit 13 acquires the correlation coefficients h will be described. Each grid profile g, which has pixel values aligned in a row, can be expressed by the following formula:

$$g=\{g_1, g_2, \ldots g_n\}$$

Similarly, the profile c for comparison has pixel values aligned in a row, and can be expressed by the following formula:

$$c=\{c_1, c_2, \ldots c_n\}$$

The grid image selecting unit 13 derives the correlation coefficients h from the following equation. The correlation coefficients h have scalar values.

$$h=(g_1c_1+g_2c_2+\ldots+g_nc_n)/(g_1^2+g_2^2+\ldots+g_n^2)^{1/2}\cdot(c_1^2+c_2^2+\ldots+c_n^2)^{1/2}$$

The grid image selecting unit 13 obtains correlation coefficients h for the seven grid profiles g, respectively. Then, the grid image selecting unit 13 selects a grid profile g having the largest correlation coefficient h, and selects a grid image G corresponding to this grid profile g. It means that the grid image selecting unit 13 selects one of the grid images G having the most similar pattern to the pattern of the shadows of the X-ray grid 5 appearing on the original image P0. The correlation coefficient h is a quotient resulting from the division of an inner product of the profiles g and c by a predetermined value. The denominator used at this time is provided in order to normalize the value of the inner product.

Next, a specific example of correlation coefficients h will be given. For example, when two profiles g and c are completely the same, the value of correlation coefficient h will be 1. As the two profiles g and c become progressively different, the correlation coefficient h approaches 0. A method of determining similarity between images using such a correlation coefficient h is called a correlational method. The subsequent description will be made on an assumption that the grid image selecting unit 13 has selected a grid image Ga from the grid images G.

<Eliminating Step S5>

The grid image selecting unit 13 outputs the selected grid image Ga to the eliminating unit 14. The eliminating unit 14 superimposes a reverse pattern of the grid image Ga on the original image P0, thereby to generate a corrected image P1 with the pattern of the shadows of the X-ray grid 5 removed from the original image P0. The grid image Ga has the same pattern as the pattern of the shadows of the X-ray grid 5 on the original image P0. By superimposing the two patterns, the shadows of the X-ray grid 5 are accurately eliminated from the original image P0. This corrected image P1 is displayed on the display unit 32 to complete the examination.

As described above, the X-ray apparatus 1 in Embodiment 1 includes the synchronous X-ray grid 5 synchronized with the arrangement of detecting elements 4a of the FPD 4. The arrangement pitch of the absorbing foil strips 5a of the X-ray grid 5 is determined based on the arrangement pitch of the detecting elements 4a. Consequently, there occurs no moire due to interference between the arrangement of the shadows of the absorbing foil strips 5a and the arrangement of the detecting elements 4a when in the most frequently used standard position. This realizes generation of X-ray images with improved visibility.

However, such synchronous X-ray grid 5 is liable to distortion of the absorbing foil strips 5a. When the absorbing foil strips 5a are distorted, it is difficult to predict a pattern of the shadows of the X-ray grid 5 appearing on the original image P0, and to remove the shadows of the X-ray grid 5 from the original image P0.

So, in Embodiment 1, a plurality of grid images G are picked up beforehand, and a grid image G most similar to the pattern of the shadows of the X-ray grid 5 appearing on the original image P0 is selected, which is used to eliminate the pattern of the shadows of the X-ray grid 5 from the original image P0. That is, according to the construction of Embodiment 1, the pattern of the shadows of the X-ray grid 5 can be removed accurately from the original image P0 after grasping in what shape the shadows of the X-ray grid 5 are reflected on the original image P0.

According to the construction of Embodiment 1, the grid images G can be picked up with increased appropriateness. When the positional relationship between the X-ray tube 3 and FPD 4 shifts in the transverse direction, a major change will occur with the pattern of the shadows of the X-ray grid 5 appearing on the original image P0. So, in the above construction, the grid images G are picked up beforehand while shifting the position of FPD 4 relative to the X-ray tube 3 in the transverse direction. Then, even if the positional relationship between the X-ray tube 3 and FPD 4 shifts in the transverse direction at the time of original image acquisition, the pattern of the shadows of the X-ray grid 5 appearing on the original image P0 is already procured as grid images G. This allows the pattern of the shadows of the X-ray grid 5 appearing on the original image P0 to be predicted accurately.

According to the construction of Embodiment 1, the grid images G can be picked up with increased appropriateness. In Embodiment 1, the grid images G are picked up with nothing but the X-ray grid 5 interposed between the X-ray tube 3 and FPD 4. Since only the shadows of the X-ray grid 5 are reflected on the grid images G, the pattern of the shadows of the X-ray grid 5 appearing on the original image P0 is expressed accurately.

According to the construction of Embodiment 1, similarity between the original image P0 and grid images G is determined without using the images per se, and is determined using profiles showing characteristics of the shadows of the X-ray grid 5 reflected on the images. The profiles according to Embodiment 1 have pixel values arranged in a row, whereby the profiles can be compared at high speed. Therefore, also in an examination in which original images P0 are picked up continuously, the shadows of the X-ray grid 5 can be removed from the original images P0 reliably.

The original image P0 has a patient image and the shadows of the X-ray grid 5 overlapping each other. When the profile of the original image P0 is used as it is for comparison of the profiles, the components of the patient image superimposed on the profile of the original image P0 will baffle a determination of similarity between the profiles. In view of such a situation, Embodiment 1 generates, from the original image profile p, a profile c for comparison without the patient image reflected on the original image P0, and uses this for comparison with the grid profiles g. In this way, a determination is made of similarity between the shadows of the X-ray grid 5 reflected on the original image P0 and the grid images G. Consequently, the shadows of the X-ray grid 5 reflected on the original image P0 can be grasped with increased reliability.

By carrying out comparison using the correlational method which obtains correlation coefficients of both profiles as in Embodiment 1, the shadows of the X-ray grid 5 reflected on the original image P0 can be grasped with increased reliability.

As is clear from the description using FIG. 7, this invention is applicable regardless of whether the distance between the FPD 4 and X-ray tube 3 is longer or shorter than the distance corresponding to the standard position in FIG. 4.

Figure 14:
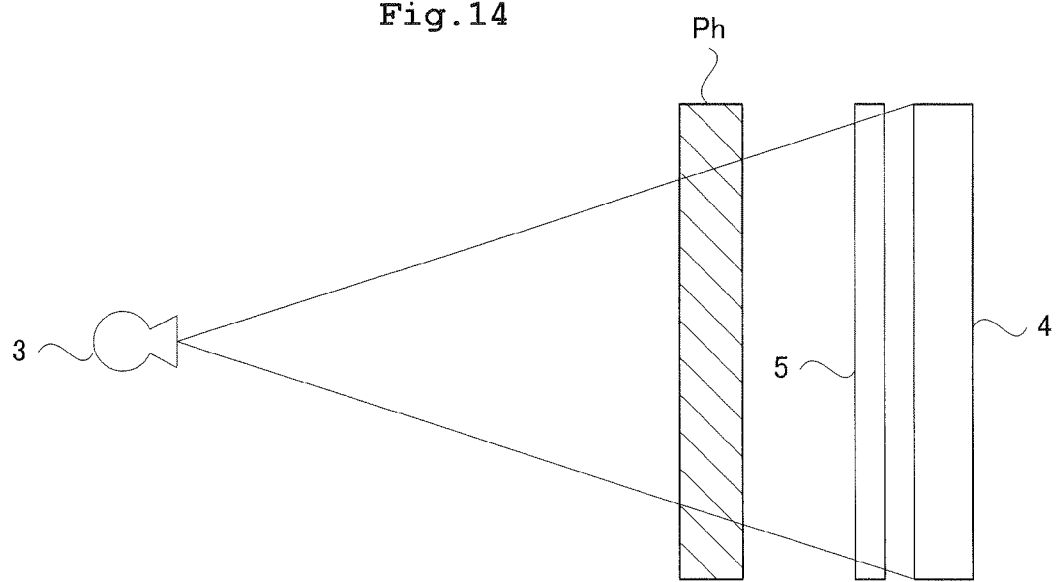
FIG. 14 is a schematic view illustrating a modification of this invention.
Figure 15:
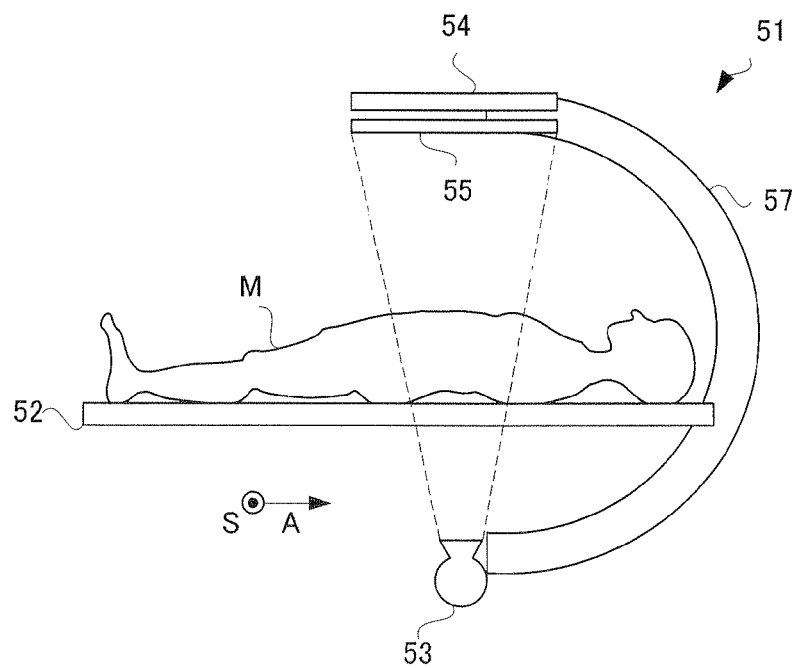
FIG. 15 is a functional block diagram illustrating a construction of a conventional X-ray apparatus.

This invention is not limited to the foregoing embodiment, but may be modified as follows:

(1) In Embodiment 1, grid images G are picked up without placing anything but the X-ray grid 5 between the X-ray tube 3 and FPD 4. This invention is not limited to this arrangement. As shown in FIG. 14, grid images G may be picked up with a plate-like phantom Ph, which generates scattered rays, placed between the X-ray tube 3 and FPD 4. The original image P0 includes scattered ray components generated from the patient M, and the pattern of the shadows of the X-ray grid 5 appearing on the original image P0 also changes under the influence of scattered rays. Therefore, the shadows of the X-ray grid 5 appearing on the original image P0 can be grasped with increased accuracy by picking up grid images G in a state of scattered rays being generated. This modified arrangement enables acquisition of grid images G that anticipate the influence of scattered rays.

(2) In the foregoing embodiment, the X-ray apparatus 1 includes one C-arm 7, but this invention is not limited to this. This invention may be applied to a biplane system having two C-arms 7.

(3) The foregoing embodiment provides a medical apparatus. This invention is applicable also to apparatus for industrial use and for the nuclear field.

(4) X-rays used in the foregoing embodiment are an example of radiation in this invention. Therefore, this invention can be adapted also for radiation other than X-rays.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus for acquiring radiological images, comprising:
    a radiation source for emitting radiation;
    a radiation detector having a detecting plane with radiation detecting elements arranged in a matrix form thereon for detecting the radiation;
    an image generating device for generating images based on detection signals outputted from the radiation detector;
    a radiation grid placed to cover the detecting plane of the radiation detector, and having absorbing foil strips extending longitudinally and arranged transversely;
    a grid image storage device for storing a plurality of grid images picked up while varying positions in a transverse direction of the radiation source and the radiation detector, without an object under examination interposed between the radiation source and the radiation detector, the grid images having shadows of the radiation grid reflected thereon;
    an original image storage device for storing an original image picked up with the object under examination interposed between the radiation source and the radiation detector, the original image having a fluoroscopic image of the object under examination and the shadows of the absorbing foil strips of the radiation grid reflected thereon;
    a selecting device for selecting one grid image having a pattern most similar to a pattern of the shadows of the radiation grid reflected on the original image, from the plurality of grid images stored in the grid image storage device; and
    an eliminating device for eliminating the shadows of the absorbing foil strips from the original image based on the grid image selected by the selecting device;
    wherein the positions of the radiation grid and the radiation detector are determined such that, when the radiation source and the radiation detector are in a standard position, an arrangement pitch of the shadows of the absorbing foil strips appearing on the detecting plane of the radiation detector as a result of a radiation beam being emitted from the radiation source and blocked by the radiation grid is an integral multiple of an arrangement pitch in a transverse direction of the radiation detecting elements, and the shadows of the absorbing foil strips appear without covering transversely adjacent pairs of the detecting elements.

2. The radiographic apparatus according to claim 1, wherein the grid images stored in the grid image storage device have been picked up while shifting the position of the radiation detector relative to the radiation source in the transverse direction.

3. The radiographic apparatus according to claim 1, wherein the grid images stored in the grid image storage device have been picked up without anything placed between the radiation source and the radiation grid.

4. The radiographic apparatus according to claim 1, wherein the grid images stored in the grid image storage device have been picked up with a phantom, which generates scattered rays, placed between the radiation source and the radiation grid.

5. The radiographic apparatus according to claim 1, further comprising:
    a profile generating device for generating profiles each having pixel values arranged in a row in the transverse direction of the radiation grid, based on images each having pixel values arranged in two dimensions;
    wherein the selecting device is arranged to select the one grid image using an original image profile generated from the original image, and grid profiles generated from the grid images.

6. The radiographic apparatus according to claim 5, wherein the profile generating device is arranged to generate an estimated profile from the original image profile when the radiation grid is not reflected on the original image, and generate a profile for comparison by subtracting the estimated profile from the original image profile, and wherein the selecting device is arranged to select the one grid image by selecting a grid profile most similar to the profile for comparison.

7. The radiographic apparatus according to claim 6, wherein the selecting device is arranged to determine similarity between the profile for comparison and the grid profiles by a correlational method.

8. The radiographic apparatus according to claim 1, further comprising a C-arm for supporting the radiation source and the radiation detector.

9. The radiographic apparatus according to claim 2, further comprising a C-arm for supporting the radiation source and the radiation detector.

10. The radiographic apparatus according to claim 3, further comprising a C-arm for supporting the radiation source and the radiation detector.

11. The radiographic apparatus according to claim 4, further comprising a C-arm for supporting the radiation source and the radiation detector.

12. The radiographic apparatus according to claim 5, further comprising a C-arm for supporting the radiation source and the radiation detector.

13. The radiographic apparatus according to claim 6, further comprising a C-arm for supporting the radiation source and the radiation detector.

14. The radiographic apparatus according to claim 7, further comprising a C-arm for supporting the radiation source and the radiation detector.

15. The radiographic apparatus according to claim 1, wherein the radiation grid is a synchronous grid with an arrangement of the absorbing foil strips synchronized with an arrangement of the detecting elements of the radiation detector.

16. The radiographic apparatus according to claim 2, wherein the radiation grid is a synchronous grid with an arrangement of the absorbing foil strips synchronized with an arrangement of the detecting elements of the radiation detector.

17. The radiographic apparatus according to claim 3, wherein the radiation grid is a synchronous grid with an arrangement of the absorbing foil strips synchronized with an arrangement of the detecting elements of the radiation detector.

18. The radiographic apparatus according to claim 4, wherein the radiation grid is a synchronous grid with an arrangement of the absorbing foil strips synchronized with an arrangement of the detecting elements of the radiation detector.

19. The radiographic apparatus according to claim 5, wherein the radiation grid is a synchronous grid with an arrangement of the absorbing foil strips synchronized with an arrangement of the detecting elements of the radiation detector.

20. The radiographic apparatus according to claim 6, wherein the radiation grid is a synchronous grid with an arrangement of the absorbing foil strips synchronized with an arrangement of the detecting elements of the radiation detector.

* * * * *